United States Patent
Zalka

(10) Patent No.: US 11,672,742 B2
(45) Date of Patent: Jun. 13, 2023

(54) DEODORANT INCLUDING AT LEAST ONE FRUIT ACID AND METHODS OF USING THE SAME

(71) Applicant: Surface Deep LLC, Roxbury, CT (US)

(72) Inventor: Alicia Zalka, Roxbury, CT (US)

(73) Assignee: Surface Deep LLC, Roxbury, CT (US)

( * ) Notice: Subject to any disclaimer, the term of this patent is extended or adjusted under 35 U.S.C. 154(b) by 20 days.

(21) Appl. No.: 16/708,252

(22) Filed: Dec. 9, 2019

(65) Prior Publication Data

US 2020/0214944 A1 Jul. 9, 2020

Related U.S. Application Data

(60) Provisional application No. 62/787,885, filed on Jan. 3, 2019.

(51) Int. Cl.
| | |
|---|---|
| A61K 8/02 | (2006.01) |
| A61K 8/99 | (2017.01) |
| A61K 8/362 | (2006.01) |
| A61K 8/365 | (2006.01) |

(52) U.S. Cl.
CPC .......... *A61K 8/0208* (2013.01); *A61K 8/362* (2013.01); *A61K 8/365* (2013.01); *A61K 8/99* (2013.01)

(58) Field of Classification Search
None
See application file for complete search history.

(56) References Cited

U.S. PATENT DOCUMENTS

| | | | |
|---|---|---|---|
| 4,112,167 A | 9/1978 | Dake et al. | |
| 5,055,216 A | 10/1991 | Johnson | |
| 5,141,803 A | 8/1992 | Pregozen | |
| 5,972,360 A | 10/1999 | Braun | |
| 6,203,810 B1 * | 3/2001 | Alemany | A41D 27/13 424/400 |
| 6,290,659 B1 | 9/2001 | Hill | |
| 6,358,516 B1 | 3/2002 | Harod | |
| 6,440,437 B1 | 8/2002 | Krzysik et al. | |
| 6,482,423 B1 | 11/2002 | Beerse et al. | |
| 6,488,943 B1 | 12/2002 | Beerse et al. | |
| 6,491,928 B1 | 12/2002 | Smith | |
| 6,613,729 B1 | 9/2003 | Cole et al. | |
| 6,685,020 B2 * | 2/2004 | Briseboi | A61F 13/551 206/440 |
| 6,753,063 B1 | 6/2004 | Pung et al. | |
| 7,482,021 B1 | 1/2009 | Tison et al. | |
| 7,592,019 B2 | 9/2009 | Drucks et al. | |
| 8,017,145 B2 | 9/2011 | Hart et al. | |
| 8,066,956 B2 | 11/2011 | Do et al. | |
| 8,632,790 B2 | 1/2014 | Gregoire et al. | |
| 8,789,231 B2 | 7/2014 | Yuan | |
| 2003/0012760 A1 | 1/2003 | Jehn-rendu et al. | |
| 2003/0031703 A1 | 2/2003 | Mcmeekin et al. | |
| 2004/0126177 A1 | 7/2004 | Puvvada et al. | |
| 2004/0176002 A1 | 9/2004 | Siegwart | |
| 2004/0258903 A1 * | 12/2004 | Eberle | A41D 27/13 428/317.9 |
| 2005/0000046 A1 | 1/2005 | Popovsky et al. | |
| 2005/0048856 A1 * | 3/2005 | Hauser | C11D 3/2079 442/59 |
| 2005/0277568 A1 | 12/2005 | Keenan et al. | |
| 2006/0110466 A1 | 5/2006 | Haizlip | |
| 2006/0210517 A1 | 9/2006 | Mower | |
| 2007/0000082 A1 | 1/2007 | Picard et al. | |
| 2007/0049512 A1 | 3/2007 | Keenan et al. | |
| 2007/0134304 A1 | 6/2007 | Aubrun-sonneville et al. | |
| 2007/0202062 A1 * | 8/2007 | Workman | A23L 29/04 424/66 |
| 2008/0014289 A1 | 1/2008 | Li | |
| 2008/0247993 A1 * | 10/2008 | Reindl | C12R 1/23 424/93.1 |
| 2008/0274147 A1 | 11/2008 | Schaeffer et al. | |
| 2009/0019656 A1 | 1/2009 | Mitchell | |
| 2009/0155325 A1 * | 6/2009 | Wenzel | A61F 13/8405 424/402 |
| 2009/0325837 A1 | 12/2009 | Mundschau et al. | |
| 2010/0028392 A1 | 2/2010 | Cawthorne et al. | |
| 2011/0083290 A1 | 4/2011 | Brooks | |
| 2011/0088711 A1 | 4/2011 | Bonafos | |
| 2011/0186076 A1 | 8/2011 | Appleton | |
| 2011/0268777 A1 | 11/2011 | Marsh et al. | |

(Continued)

FOREIGN PATENT DOCUMENTS

| | | | | |
|---|---|---|---|---|
| WO | WO-0108658 A1 * | 2/2001 | ............. | A61Q 19/10 |
| WO | WO-2016089288 A1 * | 6/2016 | ............. | A61K 8/345 |

OTHER PUBLICATIONS

Sweatman et al (https://www.ursamajorvt.com/blogs/the-blog-cabin/11-steps-to-find-the-best-all-natural-deodorant). (Year: 2018).*

(Continued)

*Primary Examiner* — Celeste A Roney

(74) *Attorney, Agent, or Firm* — Dorsey & Whitney LLP

(57) ABSTRACT

In an example, the deodorant includes a solution. The solution includes a diluent and at least one fruit acid (i.e., at least one alpha hydroxy acid). The solution may also include at least one probiotic. In an embodiment, the deodorant may also include at least one applicator that is configured to hold the solution, such as at least one pad. In an embodiment, a method of using the deodorant may include contacting the armpit (e.g., axilla) or another region of the body with the deodorant to control the body odor of the individual.

23 Claims, 1 Drawing Sheet

(56) References Cited

U.S. PATENT DOCUMENTS

| | | | |
|---|---|---|---|
| 2012/0100195 A1 | 4/2012 | Sainz et al. | |
| 2012/0301452 A1* | 11/2012 | Gueniche | A61K 8/9728 |
| | | | 424/93.45 |
| 2013/0108722 A1 | 5/2013 | Stangler et al. | |
| 2014/0212464 A1 | 7/2014 | Deckner et al. | |
| 2016/0303002 A1 | 10/2016 | Cunningham et al. | |
| 2016/0310406 A1 | 10/2016 | Nebel et al. | |
| 2017/0014652 A1 | 1/2017 | Maalouf et al. | |

OTHER PUBLICATIONS https://www.today.com/shop/glycolic-acid-deodorant-t224506 (Year: 2021).*

PH Beautiful (https://www.phbeautiful.com/pages/glycolic-acid-for-acne-treatment, 2016). (Year: 2016).*

Proactive (https://www.proactiv.com/blog/acne-skin-care-ingredients/glycolic-acid, 2017). (Year: 2017).*

Mccosmetics NY (https://www.linkedin.com/pulse/benefits-glycolic-acid-mccosmetics-ny, 2018). (Year: 2018).*

Katz et al (https://www.everydayhealth.com/beauty-pictures/the-best-ingredients-to-control-oily-skin.aspx, 2014). (Year: 2014).* https://verilyskin.com/glycolic-acid-underarms/ (Year: 2022).* https://elle.in/acids-on-underarms-benefits/#:~:text=Dr%20Uktra%20explains%20that%20glycolic,better%20it%20is%20for%20experimentation. (Year: 2022).*

Active Micro Technologies, "Leucidal SF Complete Technical Data Sheet", Version 1, Feb. 4, 2016, 4 pages.

Robey, Tracy E., "Racked—The Best Natural Deodorant is Acid", https://www.racked.com/2018/2/20/17021612/natural-deodorant-acid; (Accessed Mar. 23, 2020), Feb. 20, 2018.

Cook, Kim K. et al., "Glycolic Acid Peels", CRC Press Abstract, 1st ed. 2002, 2 pages.

Evans, R. L. et al., "Axillary skin: biology and care", 34 Int. J. of Cosmetic Sci. 389, 2012,7 pages.

Gillespie, Mary, "Glycolic Acid Problems", https://www.skin911.com/pages/glycolic-acid-prolems.html, 2022, 5 pages.

Goldsmith, Lowell A., "Physiology, Biochemistry and Molecular Biology of the Skin", vol. 2, 1448-149 (2nd ed. 1991), 3 pages.

Hengge, U.R. et al., "Adverse effects of topical glucocorticosteroids", 54 J Am. Acad. Dermatol. 2006, 1-15 pages.

Kapitany, A. et al., "Regional Differences in the Permeability Barrier of the Skin—Implications in Acantholytic Skin Diseases", 22(19) Int. J. Mol. Sci. 10428, 2021, 11 pages.

Oakley, Amanda, "Topical Formulations", DermNet NZ, https://dermnetnz.org/topics/topical-formulations, Feb. 2016, 10 pages.

Palmer, Angela, "How to Use Glycolic Acid in Your Skin Care", Very Well Health, https://www.verywellhealth.com/glycolic-acid-15774, 2022, 11 pages.

* cited by examiner

DEODORANT INCLUDING AT LEAST ONE FRUIT ACID AND METHODS OF USING THE SAME

RELATED APPLICATIONS

The present application claims priority to U.S. patent application Ser. No. 62/787,885, filed Jan. 3, 2019 entitled DEODORANT PADS, the disclosure of which is incorporated herein by reference in its entirety.

BACKGROUND

Deodorants are often applied to the body to control body odor caused by the bacterial proliferation that is present and flourishes in the presence of perspiration in armpits, feet, and other areas of the body. A subgroup of deodorants, antiperspirants, control body odor as well as prevent perspiration by affecting sweat glands. Antiperspirants are typically applied to the armpits while deodorants may also be used on other areas of the body (e.g., feet).

Deodorants are often applied in stick, spray, rollerball, or cream. Typically, deodorants include baking soda, magnesium, aluminum (e.g., aluminum salts), or other substances. Deodorants deposit a film on the individual and/or use fragrances to control the body odor.

Fruit acid is commonly used as a facial exfoliant. For example, the fruit acid may be applied to the face of an individual using pads, cotton balls, or other applicators. The fruit acid may be applied to regions of the face, avoiding eyes and lips, at concentrations greater than 7 weight %, such as about 7 weight % to about 30 weight %, due to the insensitivity of these regions of the face. Individuals with sensitive skin may remove the fruit acid a few minutes after applying the fruit acid to the skin. Fruit acid is applied to the face due to fruit acid's ability to desquamate surface skin cells from the face and treat such conditions as acne.

SUMMARY

In an embodiment, a deodorant is disclosed. The deodorant includes at least one pad defining a plurality of pores and a solution occupying at least a portion of the plurality of pores. The solution includes a diluent, at least one fruit acid, and at least one probiotic.

In an embodiment, a method of using a deodorant is disclosed. The deodorant includes at least one pad defining a plurality of pores and a solution occupying at least a portion of the plurality of pores. The solution includes a diluent, at least one fruit acid, and at least one probiotic. The method includes contacting the at least one pad against at least one armpit.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1:
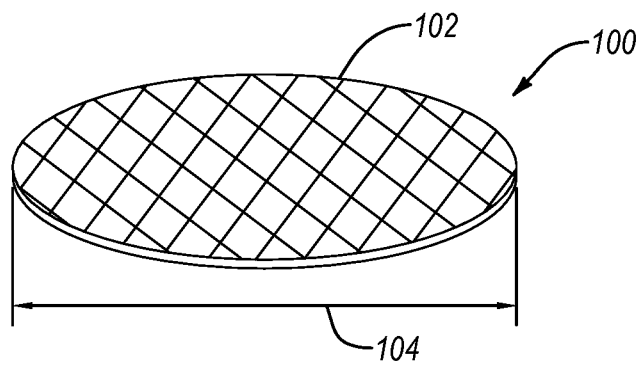
FIG. 1 is an isometric view of a deodorant that includes a pad, according to an embodiment.

The embodiments disclosed herein include deodorants and methods of using the deodorants. In an example, the deodorant includes a solution. The solution includes a diluent and at least one fruit acid (i.e., at least one alpha hydroxy acid). The solution may also include at least one probiotic. In an embodiment, the deodorant may also include at least one applicator that is configured to hold the solution, such as at least one pad. In an embodiment, a method of using the deodorant may include contacting the armpit (e.g., axilla) or another region of the body with the deodorant to control the body odor of the individual.

The diluent of the deodorant is a liquid in which the other components of the deodorant (e.g., the fruit acid, the probiotic, the applicator, etc.) are disposed. In other words, the diluent dilutes the other components of the deodorant (e.g., the diluent is a solvent). The diluent may be selected to dissolve the other components of the deodorant and/or have the other components of the deodorant suspended therein. The diluent may be the largest component of the deodorant, by weight and/or volume. The diluent is non-active, that is, has little to no effect on the function of the deodorant other than diluting the other components of the deodorant and/or substantially does not react with the other components of the deodorant. In an example, the diluent includes water since water substantially does not react with the fruit acid. In an example, the diluent may include an alcohol even though the alcohol may slightly react with the fruit acid to form water.

The solution includes at least one fruit acid because the fruit acid prevents the bacterial proliferation that produces body odor. The fruit acid may prevent the bacterial proliferation by removing at least one of the sebum deposits (i.e., the body's natural oils) or desquamated skin cells from the epidermis. The sebum deposits along with desquamated skin cells, may harbor the bacteria that cause body odor to grow. As such, removing at least one of the sebum deposits or the desquamated skin cells from the skin using the fruit acid prevents or at least inhibits the growth of the bacteria that cause body odor. The fruit acid may also prevent the bacterial proliferation by creating an environment that is inhospitable to the bacteria that cause body odor. For example, the fruit acid may do at least one of: lower the pH in and around the skin (e.g., decrease the pH of sweat) sufficiently to inhibit bacteria growth, react with chemicals that are necessary for bacteria growth, or react with the bacteria itself.

In an embodiment, the fruit acid includes glycolic acid since glycolic acid is readily available and inexpensive (which makes glycolic acid suitable for large scale deodorant manufacture), plant-based (i.e., vegan), a dermatologically safe and predictable exfoliant, colorless (e.g., will not stain clothes or be noticeable on the skin), odorless, hypoallergenic compound, and the acidity thereof is safe to leave on the intertriginous skin (i.e., skin fold). In an example, the fruit acid includes at least one of lactic acid, citric acid, malic acid, or tartaric acid instead of or in conjunction with glycolic acid. In an example, the fruit acid may include glycolic acid instead of or include more glycolic acid than the other fruit acids because glycolic acid is considered to be at least one of the more dermatologically safe and predictable exfoliants than the other fruit acids, or exhibits an acidity that is more safe to leave on the intertriginous skin than the other fruit acids.

In an embodiment, the fruit acid is provided in the solution using a natural source. Examples of natural sources of fruit acid include *acer saccharum* (sugar maple) extract, citrus *aurantium dulcis* fruit extract or other orange fruit extracts, citrus limon (lemon) fruit extract, or other citrus fruit extracts. In an embodiment, the fruit acid that is included in the solution includes a synthetic fruit acid (e.g., via a fermentative process or chemical process) or a purified fruit acid. The synthetic or purified fruit acid may include detrimental impurities (e.g., metal from the equipment used, precursor or intermediate compounds, catalysts, etc.) that the natural sources of fruit acid do not include.

The amount of the fruit acid in the solution is less than 15 weight %, such as less than 10 weight %, less than 9 weight %, less than 8 weight %, less than 7 weight %, less than 6 weight %, less than 5 weight %, less than 4 weight %, less than 3 weight %, less than 2 weight %, less than 1 weight %, or in ranges of 1 weight % to 3 weight %, 2 weight % to 4 weight %, 3 weight % to 5 weight %, 4 weight % to 6 weight %, 5 weight % to 7 weight %, 6 weight % to 8 weight %, 7 weight % to 9 weight %, 8 weight % to 10 weight %, or 9 weight % to 15 weight %. The amount of the probiotic in the solution may also be about any of the above ranges or values disclosed above. The amount of the fruit acid in the solution may depend on a number of factors.

In an embodiment, the amount of the fruit acid in the solution may be selected based on the region of the body that the solution is configured to be applied. For example, the amount of the fruit acid in the solution may be selected to be less than about 6 weight % or about 5 weight % or less when the solution is applied to the armpit. The amount of the fruit acid in the solution is selected to be less than 6 weight % or about 5 weight % or less when configured to be applied to the armpit for several reasons. For instance, the armpit includes a moist portion and a dry portion. The moist portion of the armpit includes at least one of a portion of the armpit that (in the absence of antiperspirant) is commonly moist, including (i.e., is in fluid communication with) the eccrine glands and the apocrine glands, or includes underarm hair. The dry portion of the armpit includes any region of the armpit that is not a moist portion. Generally, the dry portion of the armpits are more sensitive to (e.g., are more to be irritated by) the fruit acid than the facial skin, which limits the concentration of the fruit acid that may be applied thereto. Additionally, the dry portions of the armpit are more sensitive to the fruit acids than the moist portion which, in turn, limits the concentration of the fruit acid since, even though it is desirable to only apply the solution to the moist portion of the armpit, the solution may be inadvertently applied to the dry portion of the armpit. Additionally, the armpit is an intertriginous region (i.e., a region where two skin areas touch and/or rub against each other) of the individual which inhibits dilution of the solution and inhibits dissipation of the solution. Further, the fruit acid is more active (e.g., behaves as if the fruit acid is present at higher concentrations) when the fruit acid is applied to an intertriginous region than if the fruit acid is applied to a non-intertriginous region (e.g., facial skin). Another reason the amount of the fruit acid in the solution is selected to be less than about 6 weight % or about 5 weight % or less is because the solution may not be removed (e.g., rinsed) from the armpit, similar to facial exfoliants, since the fruit acid must remain on the armpit for the fruit acid to prevent or inhibit body odors. It is noted that the amount of the fruit acid in the solution may be greater than about 5 weight % or greater than about 6 weight %, for example, when the solution is configured to be applied to other regions of the body, such as non-intertriginous regions or regions of the individual that are less sensitive to the fruit acid than the armpit.

In an embodiment, the amount of the fruit acid in the solution may depend on the composition of the fruit acid. For example, the fruit acid may include more glycolic acid than other fruit acids since, as previously discussed, glycolic acid is generally considered to be a more dermatologically safe and predictable exfoliant than the other fruit acids or exhibits an acidity that is more safe to leave on the intertriginous skin than the other fruit acids. As such, the fruit acid may include larger amounts of glycolic acid (e.g., about 3 weight % to about 6 weight % or about 4 weight % to about 5 weight %) and significantly less amounts of other fruit acids (e.g., less than 2 weight % or less than 1 weight %) when the solution includes glycolic acid and/or at least one other fruit acid and the solution is configured to be applied to the armpit.

In an embodiment, the amount of the fruit acid in the solution depends on how frequently the solution is applied to the individual. Generally, deodorant is applied to the individual everyday over a prolonged period of time (e.g., at least a week or at least a month). The exfoliation properties of the fruit acid will, inherently, cause some damage to the skin. The amount of damage to the skin is directly proportional to the amount of fruit acid in the solution and the sensitivity of the skin to the fruit acid. Even if the amount of damage to the skin is minimal, the amount of damage to the skin may become large if the skin is unable to heal itself between applications of the deodorant. As such, the amount of the fruit acid in the solution is limited such that the amount of damage to the skin is sufficiently small that the damage may be completely or substantially completely healed between applications. Because of this, the amount of fruit acid in the solution may be selected to be less than about 6 weight %, about 5 weight % or less, when the solution is applied to the armpit since the average armpit is able to at least substantially completely heal any damage caused thereto between applications of the fruit acid. In an embodiment, as will be discussed in more detail below, the amount of the fruit acid may be selected based on the saturation level of the solution in an applicator (e.g., pad).

The solution also includes at least one probiotic. In an embodiment, the probiotic is a bacteria, fungus, ferment (e.g., bacteria ferment), or other micro-organism that has minimal effect on body odor. In an embodiment, the probiotic includes *lactobacillus, lactobacillus* ferment, *saccharomyces* ferment, *bifidobacterium*, or *vitreoscilla*.

In an embodiment, the probiotic exhibits antimicrobial properties. In an example, antimicrobial properties of the probiotic may include the ability to kill at least some of the same body odor causing bacteria as the fruit acid. In such an example, the probiotic may cause the solution to kill a greater percentage of the body odor causing bacteria than if the solution only included the fruit acid and/or may allow the solution to include a lower concentration of the fruit acid. In an example, the antimicrobial properties of the probiotic may include the ability to kill at least some of the body odor causing bacteria that are resistant to the fruit acid. In such an example, the probiotic may cause the solution to better inhibit or prevent body odor than if the solution only included the fruit acid. Examples of probiotics that exhibit antimicrobial properties include *lactobacillus, lactobacillus* ferment, *saccharomyces* ferment, *bifidobacterium*, and *vitreoscilla*.

In an embodiment, the probiotic is selected to create a beneficial (i.e., non-body odor causing) microbiome in the portion of the body (e.g., armpit) that receives the solution. For example, the fruit acid and, optionally, the probiotic may alter the microbiome of the region of the body that receives the solution since the fruit acid and, optionally, the probiotic kill and/or inhibit the growth of bacteria and other microbes. Altering the microbiome of the region of the body that receives the solution may cause unintended side effects, such as dry skin or cause rashes to develop on the region. The probiotic may mitigate the side effects caused by altering the microbiome by facilitating the growth of the microbiome. For example, the probiotic may cause the growth of a microbiome that does not include or substantially does not include bacteria that causes body odor. Examples of probiotics that create a beneficial microbiome include *lactobacillus, lactobacillus* ferment, *saccharomyces* ferment, *bifidobacterium*, and *vitreoscilla*.

In an embodiment, the probiotic is an anti-inflammatory agent exhibiting anti inflammatory properties. For example, the fruit acid exfoliates the skin which, in turn, may damage the skin (e.g., by over-exfoliating the skin). The damaged skin may cause irritation and develop into a rash. However, the anti-inflammatory agent is selected to at least calm the irritation or facilitate healing of the skin. As such, selecting the probiotic to be an anti-inflammatory agent may allow the solution to include a higher concentration of fruit acid (e.g., a solution configured for use in the armpit may include less than 3 weight % fruit acid without the skin soother, depending on the embodiment), may allow the solution to be applied more regularly to the body, allow the solution to be applied to more sensitive regions of the body (e.g., the dry region of the armpit), or mitigate the effects of inadvertently applying the solution to sensitive regions of the body (e.g., the dry portion of the armpit). Examples of probiotics that are also anti-inflammatory agents include *lactobacillus, lactobacillus* ferment, and *saccharomyces* ferment.

The amount of the probiotic that is present in the solution is less than the amount of fruit acid that is present in the solution. For example, the amount of the probiotic that is present in the solution may be less than 5 weight %, less than 4.5 weight %, less than 4 weight %, less than 3.5 weight %, less than 3 weight %, less than 2.5 weight %, less than 2 weight %, less than 1.5 weight %, less than 1 weight %, less than 0.75 weight %, less than 0.5 weight %, less than 0.25 weight %, less than 0.1 weight %, or in ranges of 0.1 weight % to 0.5 weight %, 0.25 weight % to 0.75 weight %, 0.5 weight % to 1 weight %, 0.75 weight % to 1.5 weight %, 1 weight % to 2 weight %, 1.5 weight % to 2.5 weight %, 2 weight % to 3 weight, 2.5 weight % to 3.5 weight %, 3 weight % to 4 weight %, or 3.5 weight % to 5 weight %. The amount of the fruit acid in the solution may also be about any of the above ranges or values disclosed above. The amount of the probiotic that is present in the solution may be selected based on a variety of factors. In an example, the amount of the probiotics that are present in the solution may depend on whether the probiotic exhibits antimicrobial properties, creates a beneficial microbiome, is an anti-inflammatory agent, or any combinations thereof. In an example, the amount of the probiotics that are present in the solution may depend on the amount of the fruit acid that is present in the solution. For example, increasing the amount of fruit acid in the solution may necessitate an increase in the amount of probiotic that is present in the solution, and vice versa. In an example, the amount of the probiotic that is present in the solution may depend on the saturation level of the solution in the applicator, as discussed in more detail below.

Optionally, the solution may include one or more components in addition to the at least one fruit acid and the at least one probiotic. In an embodiment, the solution includes at least one pH adjuster. The pH adjuster is selected to control the pH of the solution, such as when a component of the solution (other than the fruit acid) is not pH neutral or the pH of the solution needs to be adjusted to be safe to leave on the intertriginous skin. Examples of the pH adjuster includes sodium hydroxide and ammonium hydroxide. In an embodiment, the solution includes at least one anti-inflammatory agent. As previously discussed, the probiotic may be an anti-inflammatory agent. However, it may be beneficial to include an anti-inflammatory agent other than a probiotic, for example, when the probiotic is not a skin soother or the probiotic, by itself, is not sufficient. Examples of anti-inflammatory agents includes Vaccinium myrtillus fruit extract, Hamamelis virginiana extract, Cocos nucifera fruit extract, and allantoin. In an embodiment, the solution includes at least one antiseptic and/or antimicrobial agent. In an embodiment, the solution may include a chemical exfoliant in addition to the fruit acids. An example of a chemical exfoliant includes at least one beta hydroxy acid. In an embodiment, the solution may include at least one humectant, such as glycerin, to act as an emollient. In an embodiment, the solution may include at least one surfactant, emulsifier, and/or stabilizer, such as at least one of sodium lauryl glucose, lauryl glucoside, PPG-5 Ceteth-20, polysorbate 20. In an embodiment, the solution may include at least one preservative, such as sodium benzoate or imidazolidinyl urea, which may prevent bacteria growth in the solution and/or preserve the probiotic.

Optionally, the solution may be substantially free of one or more components. In an embodiment, the solution is free from non-essential oil fragrances since such fragrances may cause allergic reactions. In an embodiment, the solution is free from film-forming components that are commonly used in conventional deodorants and antiperspirants. Examples of film-forming components includes aluminum salts, alum, charcoal, magnesium hydroxide, polymers, etc.

The deodorant (i.e., the solution) is configured to be applied to a region of the body. For example, as previously discussed, the deodorant may be applied to the armpit. It is noted that the deodorant may be configured to be applied to other regions of the body. For example, the deodorant may be configured to be applied to the genitals, the perineum, the feet, the popliteal fossa (a.k.a., kneepit), the antecutibal fossa (a.k.a., elbow pit), other intertriginous skin regions, the neck, the back, the stomach, or the limbs.

The deodorant may include at least one applicator that is configured to apply the solution to the body. In an embodiment, the applicator includes at least one pad. FIG. 1 is an isometric view of a deodorant 100 that includes a pad 102, according to an embodiment. The deodorant 100 includes a solution. The solution may include any of the solutions disclosed herein.

The pad 102 defines a plurality of pores (e.g., void space), configured to contain and allow application of the solution therefrom. In an example, the pad 102 includes a mass of fibers (e.g., woven or non-woven fibers) and the pores are the space between the fibers. In an example, the pad 102 is a foam and the pores are the void space. In an example, the plurality of pores of the pad 102 may be interconnected such that the pores form passageways through the pad 102 or the plurality of pores of the pad 102 are not interconnected. The pores of the pad 102 may exhibit an average pore size that is greater than 1 µm, greater than 2 µm, greater than 3 µm, greater than 4 µm, greater than 5 µm, greater than 6 µm, greater than 7.5 µm, greater than 10 µm, greater than 15 µm, greater than 20 µm, greater than 40 µm, greater than 50 µm, greater than 100 µm, greater than 250 µm, less than 500 µm, less than 200 µm, less than 100 µm, less than 50 µm, less than 40 µm, less than 20 µm, less than 10 µm, less than 7.5 µm, less than 5 µm, or in ranges of 1 µm to 500 µm, 1 µm to 50 µm, 1 µm to 10 µm, 2.5 µm to 7.5 µm, 10 µm to 40 µm, 10 µm to 100 µm, or 75 µm to 250 µm. The average pore size of the pad 102 may also be about any of the above ranges or values disclosed above. At least some of the plurality of pores of the pad 102 are at least partially occupied by the solution. The pad 102 may be configured to hold the solution in the pores thereof while a user of the deodorant handles the pad 102. The pad 102 may release some of the solution onto the body of the user when the pad 102 contacts a region (e.g., armpit) of the user.

The pad 102 may exhibit a dimension 104. When the pad 102 exhibits a generally circular shape (e.g., the pad 102 is a cylinder with minimal thickness), the dimension 104 of the pad 102 is the diameter of the pad 102. When the pad 102 exhibits a non-circular shape (e.g., generally rectangular shape), the dimension 104 is at least one of a maximum lateral dimension of the pad 102 or is a dimension measured perpendicularly from an edge of the pad 102 to an opposing edge of the pad 102. The dimension 104 of the pad 102 may be greater than 3 cm, greater than 4 cm, greater than 5 cm, greater than 5.5 cm, greater than 6 cm, greater than 6.5 cm, greater than 7 cm, greater than 10 cm, greater than 15 cm or in ranges of 3 cm to 15 cm, 4 cm to 8 cm, 5 cm to 7 cm, 6 cm to 8 cm, or 6 cm to 7 cm. The dimensions 104 of the pad 102 may also be about any of the above ranges or values disclosed above. The dimension 104 of the pad 102 may be selected based on a number of factors. In an embodiment, the dimension 104 may depend on the region of the body that the pad 102 is configured to contact. For example, when the pad 102 is configured to contact the armpit, the dimension 104 of the pad 102 may be greater than 6 cm. It is currently believed by the inventors that pads exhibiting a dimension less than 6 cm, when used by the unskilled user, are unlikely to contact substantially all of the armpit which may allow the body odor causing bacteria to grow in uncontacted portions of the armpit. When the dimension 104 is greater than 7 cm, it may be difficult to avoid contacting the dry regions of the armpit with the pad 102. In an embodiment, the dimensions 104 of the pad 102 may be selected to be large enough to be gripped using two fingers (e.g., greater than about 3 cm) or three fingers (e.g., greater than about 5 cm).

The pad 102 may exhibit any suitable shape. In an embodiment, as illustrated, the pad 102 may exhibit a generally circular shape which may facilitate applying the solution to the generally curved regions of the armpit. In an embodiment, the pad 102 may exhibit a generally rectangular (e.g., square) shape which may allow the pad 102 to more completely occupy certain types of packaging (e.g., the package 210 of FIG. 2). In an embodiment, the pad 102 may define a cutout which may facilitate removing the pad 102 from a container that includes a plurality of pads 102.

The function of the pad 102 includes holding the solution therein. Optionally, the pad 102 is configured to exfoliate the skin. For example, the pores and the surface texture of the pad may be configured and selected to exfoliate and remove sebum from the body. The material selection of the pad 102 may depend on the desired function of the pad 102. In an example, the pad 102 may be selected to include a hydrophilic material which allows that pad 102 to retain the solution. Examples of hydrophilic materials include rayon (i.e., regenerated cellulose derived from plant sources), wool, cotton, linen, paper, bamboo, lyocell, other natural fibers, or polypropylene. In an example, the pad 102 may be selected to exfoliate the skin (i.e., the surface of the pad 102 can be configured as a mechanical exfoliant) which may enhance the deodorant's 100 ability to prevent or inhibit body odor by removing sebum deposits and desquamated skin cells from the epidermis. The ability of the pad 102 to exfoliate the skin may depend on the surface roughness of the pad 102 (e.g., caused by the pores and the surface features of the pad 102), and other characteristics such as stiffness of the surface features of the pad 102 (size and roughness of the fibers of the pad 102). For instance, increasing the surface roughness of the pad 102 may improve the pad's 102 ability to exfoliate the skin. Examples of materials that can exfoliate the skin include rayon, cotton, linen, bamboo, lyocell, paper, and polypropylene. In an example, the pad 102 is configured to be biodegradable (e.g., made from biodegradable material(s)) since the pad 102 may be configured to be disposed of after a single use and using the deodorant 100 daily may result in a significant amount of waste. Examples of materials that are biodegradable includes rayon, wool, cotton, bamboo, or paper.

The ability of the pad 102 to hold the solution and the ability of the pad 102 to exfoliate the skin may depend on the gram per square meter ("GSM") of the pad 102. The GSM of the pad 102 is directly related to the density, thickness, and porosity of the pad 102. In an example, decreasing the GSM of the pad 102 may increase the number of pores in the pad 102 thereby increasing the amount of the solution that may be held within the pad 102 and may increase the surface roughness of the pad 102. In an example, increasing the GSM of the pad 102 may increase the thickness of the pad 102 which, in turn, may increase the rigidity of the pad 102. In either example, the pad 102 may exhibit a GSM of at least 20 GSM, at least 50 GSM, at least 80 GSM, at least 100 GSM, at least 120 GSM, at least 150 GSM, at least 200 GSM, at least 300 GSM, at least 500 GSM, at least 1000 GSM, less than 1250 GSM, less than 750 GSM, less than 350 GSM, less than 200 GSM, less than 150 GSM, less than 100 GSM, or in ranges of 25 GSM to 300 GSM, 50 GSM to 1000 GSM, 50 GSM to 200 GSM, 75 GSM to 150 GSM, 50 GSM to 90 GSM, 70 GSM to 110 GSM, or 80 GSM to 100 GSM. The GSM that the pad 102 exhibits may also be about any of the above ranges or values disclosed above. It is currently believed by the inventors that a pad 102 exhibiting any of the above GSM is able to hold a sufficient amount of the solution therein and, optionally, may allow the pad 102 to be an efficient exfoliant.

As used herein, the specific saturation refers to the amount of the solution that is present in the pad. The specific saturation is a percentage and is calculated using the equation SS=(WS/WP)*100, where SS is the specific saturation, WS is the weight of the solution in the pad 102, and WP is the weight of the pad 102. In an embodiment, the specific saturation is greater than 100%, greater than 200%, greater than 300%, greater than 400%, greater than 500%, greater than 600%, greater than 700%, greater than 800%, greater than 900%, greater than 1000%, or in ranges of 100% to 300%, 200% to 400%, 300% to 500%, 400% to 600%, 500% to 700%, 600% to 800%, 700% to 900%, or 800% to 1000%. The specific saturation may also be about any of the above ranges or values disclosed above. The specific saturation may be selected based on a number of factors. In an example, the specific saturation is selected based on the amount of the fruit acid that is present in the pad 102. For instance, the specific saturation may be selected to be about 100% to about 300% when the amount of the fruit acid in the solution is greater than 6 weight % though, even at such low specific saturation, the fruit acid may still cause irritation in the armpit. Likewise, the specific saturation may be selected to be greater than 400% when the amount of the fruit acid in the solution is equal to or less than about 6 weight % and greater than 500% when the amount of the fruit acid in the solution is equal to or less than about 5 weight %. In an example, the specific saturation may be selected based on the size of the area that the deodorant 100 is configured to be applied. For instance, the specific saturation may be selected to be greater than 300% if the deodorant 100 is configured to be applied to a single armpit or greater 500% if the deodorant 100 is configured to be applied to two armpits. In an example, the specific saturation may be selected based on the sensitivity of the skin that the deodorant 100 is configured to be applied. For instance, when the deodorant is configured to be applied to the armpit, the inventors believe that the specific saturation should be less than about 700% when the solution includes 6 weight % or less fruit acid or, more specifically, 5 weight % or less fruit acid to avoid irritation to the skin when the deodorant is applied to the armpit daily over a prolonged period of time (e.g., over at least one week or over at least a month).

Figure 2:
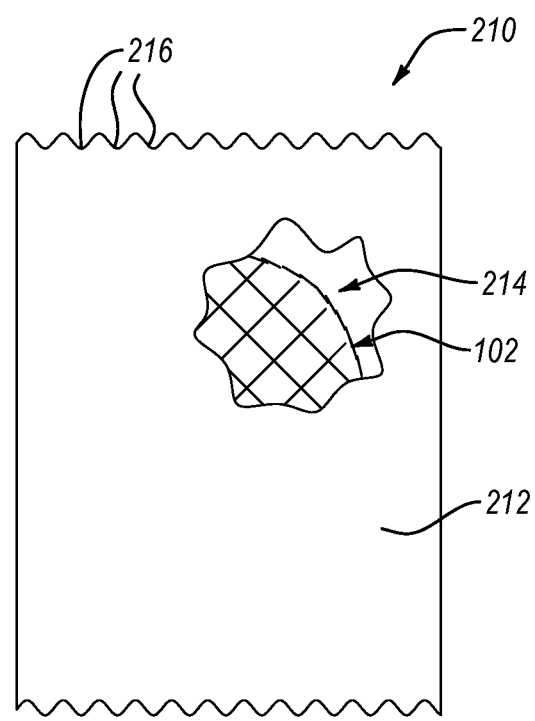
FIG. 2 is a front view of a package with a cutaway illustrating the pad of FIG. 1, according to an embodiment.

The pad 102 may be individually packaged. FIG. 2 is a front view of a package 210 with a cutaway illustrating the pad 102 of FIG. 1, according to an embodiment. The package 210 may include one or more panels 212 (e.g., film, rigid wall, etc.) that define a chamber 214. The chamber 214 may be substantially fluid tight. A single pad 102 may be disposed in the chamber 214. The pad 102 may be the same or substantially similar to any of the pads disclosed herein. In an embodiment, the package 210 may include one or more stress concentrators 216 that facilitate opening of the package 210. The stress concentrators 216 may include one or more zigzagged edges (as shown), one or more perforations, etc.

Individually packaging the pad 102 (i.e., the package 210 includes a single pad 102) has several benefits. In an example, individually packaging the pad 102 allows the specific saturation of the pad 102 to be maintained. For instance, shipping and handling of the package 210 may cause the solution to leave the pad 102. However, since the pad 102 occupies a large portion of the chamber 214, the solution is likely to reenter the pad 102. In an example, individually packaging the pad 102 facilitates usage of the pad 102 at various locations. For instance, it may be easier to throw one or a few packages 210 into a bag that is taken on vacation or to the gym than a large container that includes a plurality of pads 102 since the package 210 is smaller.

Figure 3:
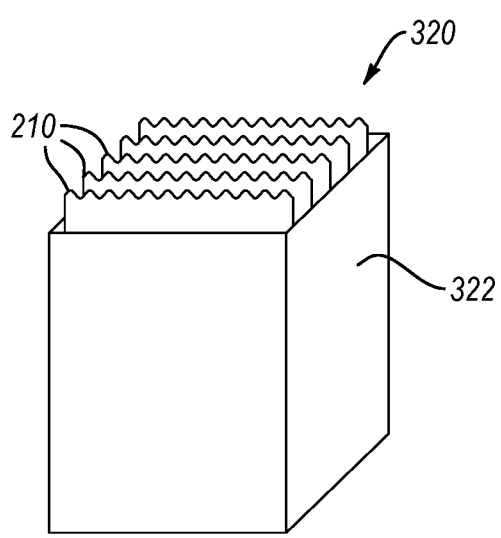
FIG. 3 is an isometric view of a group that includes a plurality of packages, according to an embodiment.

In an embodiment, the package 210 is sold individually. In an embodiment, the package 210 may form part of a group. For example, FIG. 3 is an isometric view of a group 320 that includes a plurality of packages 210, according to an embodiment. The group 320 includes a container 322 (e.g., box). The container 322 is configured to hold a plurality of packages 210. The packages 210 may be the same or similar to any of the packages disclosed herein. The container 322 may be open (as illustrated), may include a lid, or may be closed.

In an embodiment, the pads 102 may be stored within a package that includes a plurality of pads instead of a single pad. For example, the package that includes a plurality of pads may include the wrapper-type package illustrated in FIG. 2, may include a rigid package with a twist on lid, or any other suitable package. Storing a plurality of pads in a single package may decrease the volume required to store the plurality of pads than if each of the plurality of pads are individually packaged. However, storing the plurality of pads in the same container may cause at least one or some of the pads 102 (e.g., the gravimetrically lowest pad) to have a higher specific saturation than other pads 102 or result in premature drying of pads 102 that are not initially used.

It is noted that the applicator of the deodorant does not have to be a pad as discussed above. In an example, the applicator of the deodorant may be a sprayer having a reservoir that holds the solution and a nozzle connected to the reservoir that is configured to spray the solution. In an example, the applicator of the deodorant is an aerosol can. In an embodiment, the deodorant does not include an applicator. Instead, the solution is stored in a reservoir and the solution may be poured directly onto the skin or poured onto an applicator (e.g., cotton swab) and the applicator is used to apply the solution to the skin.

The methods of using any of the deodorants disclosed herein includes applying the solution to at least one region of the body. The method of using the deodorant may depend on the applicator of the deodorant. In an embodiment, when the deodorant includes a pad, the method may include opening a package that includes the pad and removing the pad from the package. The method may then include gripping the pad and contacting the pad against the region of the body to apply the solution to the region of the body. Contacting the pad against the region of the body may include pressing the pad against the region of the body to squeeze more of the solution from the pad. In an embodiment, when the deodorant includes a sprayer or an aerosol can, the method may include directing the nozzle of the deodorant towards the region of the body and dispersing the solution towards the region such that the solution is applied to the region of the body. In an embodiment, when the deodorant does not include the applicator, the method may include pouring the solution from a reservoir. The solution may be directly poured onto the region of the body or may be poured onto a separate applicator and then the solution is applied to the region of the body using the applicator.

The method of using the deodorant may also depend on the region of the body to which the deodorant is applied. In an example, the region of the body includes the armpit. In such an example, the method may include applying the deodorant to the moist portion of the armpit (e.g., contacting the pad against the moist portions of the armpit). The method may also include substantially avoiding applying the deodorant to the dry regions of the armpit (e.g., avoid contacting the pad against the dry portion of the armpit) to avoid irritating the dry portion of the armpit. It is noted that substantially avoiding the dry region of the armpit may be difficult, especially when the user of the deodorant is not a skilled practitioner and, thus, it is expected that some of the solution will be applied to the dry region of the armpit. In an example, the region of the body may include the feet, limbs, stomach, perineum, scrotum, anal region, back, or neck region of the body. In such an example, the method may include applying the solution to the particular region of the body. The method may also include substantially avoiding regions of the body that the solution is not configured to be applied since applying the solution to these regions may be ineffective or cause irritation.

In an embodiment, the method of using the deodorant includes contacting a pad against the region of the body such that the applicator does not exfoliate and/or remove sebum and desquamated skin cells from the region of the body. In an embodiment, the method of using the deodorant includes contacting the pad (e.g., a pad that is configured to exfoliate and/or remove sebum deposits and desquamated skin cells) against the region of the body such that the pad exfoliates and/or removes sebum and desquamated skin cells from the region of the body. In such an embodiment, the method may include rubbing the pad against the region of the body. The pad may exfoliate the region of the body due to the surface roughness and/or the stiffness of the surface features of the pad. Further, the pad may remove the exfoliated sebum deposits and desquamated skin cells by attaching the exfoliated sebum and desquamated skin skins to the surface of the pad (e.g., via friction, electrostatic attraction, mechanical attachment), by disposing the exfoliated sebum and desquamated skin cells in the pores of the pad, or otherwise wiping the exfoliated sebum deposits and desquamated skin cells from the region of the body.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations, as will be understood by a person having ordinary skilled in the art. In typical examples, when the term of degree indicates quantity, a person having ordinary skill in the art may interpret the term of degree to mean±5%, or ±2%, for example, as appropriate. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

I claim:

1. A daily-use armpit deodorant, comprising:
at least one pad defining a plurality of pores; and
a solution occupying at least a portion of the plurality of pores, the solution comprising:
   a diluent; and
   a body odor inhibitor including at least one fruit acid and at least one probiotic, the at least one fruit acid present at about 3 weight % to about 6 weight % of the solution;
   wherein the solution is free from film-forming components; and
wherein the deodorant is configured to be applied daily to at least one armpit.

2. The deodorant of claim 1, wherein the plurality of pores and surface features of the at least one pad are configured to exfoliate and remove sebum and desquamated skin cells when the at least one pad rubs against a region of a body.

3. The deodorant of claim 1, wherein the at least one pad is formed from rayon.

4. The deodorant of claim 1, wherein the at least one pad exhibits a dimension that is at least 60 mm, wherein the dimension is at least one of:
the greatest lateral dimension of the at least one pad; or
measured perpendicularly from one edge of the at least one pad to an opposing edge of the at least one pad.

5. The deodorant of claim 1, wherein the at least one pad exhibits about 50 grams per square meter to about 1000 grams per square meter.

6. The deodorant of claim 1, wherein the at least one fruit acid includes glycolic acid.

7. The deodorant of claim 1, wherein the at least one fruit acid includes at least one of lactic acid or citric acid.

8. The deodorant of claim 1, wherein the at least one fruit acid includes a natural source of the at least one fruit acid.

9. The deodorant of claim 1, wherein the at least one fruit acid is present at about 4 weight % to about 5 weight % of the solution.

10. The deodorant of claim 1, wherein the at least one probiotic includes a bacteria ferment.

11. The deodorant of claim 1, wherein the at least one probiotic exhibits at least one of one or more antimicrobial properties or has anti-inflammatory properties.

12. The deodorant of claim 1, wherein the at least one probiotic includes *lactobacillus* or *lactobacillus* ferment.

13. The deodorant of claim 1, wherein the at least one probiotic includes *saccharomyces* ferment.

14. The deodorant of claim 1, wherein a specific saturation of the fruit acid in the at least one pad is at least about 500%.

15. The deodorant of claim 1, wherein the solution is substantially free of non-essential oil fragrances.

16. The deodorant of claim 1, wherein the at least one pad is formed from biodegradable material.

17. The deodorant of claim 1, further comprising at least one package enclosing the at least one pad.

18. The deodorant of claim 17, wherein the at least one package includes a plurality of packages, the at least one pad includes a plurality of pads, and wherein each of the plurality of packages encloses a single one of the plurality of pads; and
further comprising a container that holds the plurality of the packages therein.

19. A method of using the deodorant of claim 1, the method comprising contacting the at least one pad against at least one armpit.

20. The method of claim 19, wherein contacting the at least one pad against the at least one armpit includes rubbing the at least one pad against the at least one armpit to exfoliate and remove sebum deposits and desquamated skin cells from the at least one armpit.

21. The method of claim 19, wherein contacting the at least one pad against the at least one armpit includes:
contacting the at least one pad against a moist portion of the at least one armpit; and
wherein the moist portion of the at least one armpit includes regions of the at least one armpit that are at least one of typically continually moist, fluidly coupled to the eccrine glands and the apocrine glands, or have underarm hair.

22. A deodorant, comprising:
at least one pad defining a plurality of pores; and
a solution occupying at least a portion of the plurality of pores, the solution comprising:
   a diluent; and
   a body odor inhibitor including glycolic acid and at least one probiotic, the glycolic acid present at about 4 weight % to about 5 weight % of the solution and the at least one probiotic present at about 0.1 weight % to about 5 weight % of the solution;
   wherein the solution is free from film-forming components.

23. The method of claim 19, wherein the contacting the at least one pad against the at least one armpit is performed daily for a plurality of days without irritating the skin of the at least one armpit.

* * * * *